(12) United States Patent
Chang et al.

(10) Patent No.: US 6,342,623 B1
(45) Date of Patent: Jan. 29, 2002

(54) PROCESS FOR CO-PRODUCTION OF DIALKYL CARBONATE AND ALKANEDIOL

(75) Inventors: Clarence D. Chang, Princeton; Larry E. Hoglen, Mickleton; Zhaozhong Jiang, Thorofare, all of NJ (US); Rene B. LaPierre, Guilford, CT (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/498,788

(22) Filed: Feb. 4, 2000

(51) Int. Cl.$^7$ .......... C07C 69/96; C07C 68/06; C07C 31/18; C07C 31/02

(52) U.S. Cl. .......... 558/277; 558/276; 558/275; 568/852; 568/902

(58) Field of Search .......... 558/277; 568/852, 568/902

(56) References Cited

U.S. PATENT DOCUMENTS

| | | | |
|---|---|---|---|
| 3,642,858 A | 2/1972 | Frevel et al. | 552/277 |
| 4,062,884 A | 12/1977 | Romano et al. | 558/277 |
| 4,181,676 A | 1/1980 | Buysch et al. | 558/277 |
| 4,391,739 A | 7/1983 | Chu | 252/455 Z |
| 4,434,105 A | 2/1984 | Buysch et al. | 558/277 |
| 4,661,609 A | 4/1987 | Knifton | 558/277 |
| 4,686,274 A | 8/1987 | Harris et al. | 528/196 |
| 4,691,041 A | 9/1987 | Duranleau et al. | 558/277 |
| 4,895,970 A | 1/1990 | Harris | 558/248 |
| 5,015,753 A | 5/1991 | Harris | 558/260 |
| 5,218,135 A | 6/1993 | Buysch et al. | 558/277 |
| 5,231,212 A | 7/1993 | Buysch et al. | 558/277 |
| 5,292,980 A | 3/1994 | Dessau | 585/866 |
| 5,387,708 A | 2/1995 | Molzahn et al. | 558/277 |
| 5,391,803 A | 2/1995 | King et al. | 558/277 |
| 5,430,170 A | 7/1995 | Urano et al. | 558/277 |
| 5,436,362 A | 7/1995 | Kondoh et al. | 558/277 |
| 5,489,703 A | 2/1996 | Pacheco et al. | 558/277 |
| 5,498,743 A | 3/1996 | Shih et al. | 558/277 |
| 5,663,480 A | 9/1997 | Tsuneki et al. | 558/270 |
| 5,847,189 A | 12/1998 | Tojo et al. | 558/277 |

FOREIGN PATENT DOCUMENTS

| | | | |
|---|---|---|---|
| EP | 0 478 073 A2 | 9/1991 | |
| JP | 3[1991]-44354 | 2/1991 | |
| JP | 4-103561 | * 4/1992 | 558/277 |
| JP | 6[1994]-107601 | 4/1994 | |
| WO | WO 00 73256 A | 12/2000 | |

OTHER PUBLICATIONS

Chang, C.D., Handbook of Heterogenous Catalysis, Wiley–VCH:Weinheim, Germany, vol. 4, Chapter 3.7 (1997).

Yagi, F., Kanuka, N., Tsuji, H., Nakata, S., Kita, H. and Hattori, H., "133Cs and 23Na MAS NMR studies of zeolite X containing cesium," Microporous Materials 9:229–235(1997).

Skibsted, J., Vosegaard, T., Bildsøe, H. and Jakobsen, H.J., "133Cs chemical Shielding Anisotropics and Quadrupole Couplings from Magic–Angle Spinning NMR of Cesium Salts," J. Phys. Chem., 100:14872–14881(1996).

Knifton, J.F. and Duranleau, R.G., "Ethylene Glycol–Dimethyl Carbonate Cogeneration," J. of Molecular Catalysis 67:389–399(1991).

Watanabe, Y. and Tatsumi T., "Hydrotalcite–type Materials as Catalysts for the Synthesis of Dimethyl Carbonate from Ethylene Carbonate and Methanol1," Microporous and Mesoporous Materials 22:399–407(1998).

* cited by examiner

Primary Examiner—Floyd D. Higel
(74) Attorney, Agent, or Firm—Malcolm D. Keen; Louis N. Moreno

(57) ABSTRACT

A method is provided for co-producing dialkyl carbonate and alkanediol by reacting alkylene carbonate with alkanol in the presence of an amorphous aluminosilicate catalyst containing alkali metal, alkaline earth metal, or a combination thereof.

10 Claims, No Drawings

PROCESS FOR CO-PRODUCTION OF DIALKYL CARBONATE AND ALKANEDIOL

BACKGROUND

This invention relates to a method of co-producing dialkyl carbonate and alkanediol and, in particular, to a method of co-producing dialkyl carbonate and alkanediol through the use of an amorphous aluminosilicate catalyst containing alkali and/or alkaline earth metal.

Various homogeneous catalysts have been proposed for carbonate transesterification. For example, U.S. Pat. Nos. 3,642,858 and 4,181,676 disclose the preparation of dialkyl carbonates by transesterifying alkylene carbonates with alcohols in the presence of alkali metals or alkali metal compounds without the use of a support material. U.S. Pat. No. 4,661,609 teaches the use of a catalyst selected from the group consisting of zirconium, titanium and tin oxides, salts or complexes thereof.

Commercial use of homogeneous catalysts is restricted because separation of the catalyst from the unconverted reactants and organic product can be difficult. Because the transesterification is an equilibrium reaction, in an attempt to isolate the intended dialkyl carbonate by distillation of the reaction liquid without advance separation of the catalyst, the equilibrium is broken during the distillation and a reverse reaction is induced. Thus, the dialkyl carbonate once formed reverts to alkylene carbonate. Furthermore, due to the presence of the homogenous catalyst, side reactions such as decomposition, polymerization, or the like concurrently take place during the distillation which decrease the efficiency.

Various heterogenous catalysts have also been proposed for carbonate transesterification. The use of alkaline earth metal halides is disclosed in U.S. Pat. No. 5,498,743. Knifton, et al., "Ethylene Glycol-Dimethyl Carbonate Cogeneration," *J. Molec. Catal.* 67:389–399 (1991) disclose the use of free organic phosphines or organic phosphines supported on partially cross-linked polystyrene. U.S. Pat. No. 4,691,041 discloses the use of organic ion exchange resins, alkali and alkaline earth silicates impregnated into silica, and certain ammonium exchanged zeolites. U.S. Pat. No. 5,430,170 discloses the use of a catalyst containing a rare earth metal oxide as the catalytically active component. The use of $MgO/Al_2O_3$ hydrotalcites is disclosed in Japanese Unexamined Patent Application 3[1991]-44,354. The use of MgO is disclosed in Japanese Unexamined Patent Application 6[1994]-107,601. The use of zeolites ion-exchanged with alkali metal and/or alkaline earth metal, thereby containing a stoichiometric amount of metal, are disclosed in U.S. Pat. No. 5,436,362.

Inorganic heterogenous catalysts generally possess thermal stability and easy regeneration. However, these catalysts, including the zeolites containing a stoichiometric amount of alkali or alkaline earth metal, generally demonstrate low activity and/or selectivity and are unsatisfactory for commercial application.

Polymer supported organic phosphines and ion exchange resins show high activity and good to excellent selectivity in transesterification reaction between alkylene carbonate and alkanol; however, these polymeric materials do not appear very stable and gradually lose catalytic activity, especially at relatively high temperatures.

Thus, there remains a need for a method of transesterifying alkylene carbonate with alkanol to co-produce dialkyl carbonate and alkanediol that will provide higher feed conversion and product selectivity over a wide temperature range.

SUMMARY OF INVENTION

A method is provided for co-producing dialkyl carbonate and alkanediol by reacting alkylene carbonate with alkanol in the presence of an amorphous aluminosilicate catalyst which includes alkali and/or alkaline earth metal. The preferred alkylene carbonate is ethylene carbonate and the preferred alkanol is methanol.

Preferred alkali metals include potassium, sodium, cesium, or a combination thereof Cesium is most preferred.

In the method of the invention, the alkali metal, alkaline earth metal, or combination thereof can be present in the catalyst either in a stoichiometric amount or in excess of a stoichiometric amount. In a preferred embodiment, the alkali metal, alkaline earth metal, or combination thereof is present in the catalyst in an amount of about 0.1 to about 50 wt %. It is also preferred that the catalyst utilized in the method of the invention have a surface area above 100 $m^2/g$.

In a separate embodiment, the catalyst utilized in the method of the invention is supported on a substrate.

The process conditions of the method of the invention include a reaction temperature of about 20° C. (68° F.) to about 300° C. (572° F.), a reaction pressure of about 14 to about 4000 psig, a liquid hourly space velocity of about 0.1 to 40 $hr^{-1}$, and a molar ratio of alkanol to alkylene carbonate of about 1–20.

Unlike polymer catalysts such as ion exchange resins, the alkali and/or alkaline earth metal exchanged amorphous aluminosilicate catalysts used in the method of the invention are thermally stable and regenerable. The combination of high catalytic activity and selectivity in a wide temperature range, and excellent thermal stability and regenerability of the catalysts, render them suitable for commercial use in co-producing organic carbonate and alkanediol through ester exchange reaction. Also, the general availability and low cost of the catalysts could significantly improve the process economics.

The organic carbonates produced by the method of the invention, dimethyl carbonate in particular, have potential application as "green" replacements for phosgene that is used mainly in manufacture of polyurethane and polycarbonate resins. Dimethyl carbonate can also be used as a fuel additive and methylating agent in fine chemical synthesis.

DETAILED DESCRIPTION OF INVENTION

In accordance with the present invention, a method is provided for the co-production of dialkyl carbonate and alkanediol through the transesterification of alkylene carbonate with alkanol using an amorphous aluminosilicate catalyst which includes alkali metal, alkaline earth metal, or a combination thereof Generally, all alkylene carbonates can be used as a reactant in this invention. However, lower alkylene carbonate such as ethylene carbonate, propylene carbonate, butylene carbonate or the like is preferred; ethylene carbonate or propylene carbonate is most preferred.

Generally, all alkanol reactants can be used, provided the alkanol reacts with cyclocarbonate to produce the dialkyl carbonate and alkanediol product. However, an aliphatic or aromatic alkanol having 1 to 10 carbon atoms is preferably used. For example, methanol, ethanol, n-propanol, iso-propanol, n-butanol, iso-butanol, secondary butanol, tertiary butanol, allyl alcohol, pentanol, cyclo-hexanol, benzyl alcohol, 2-phenyl ethyl alcohol, 3-phenyl propyl alcohol, 2-methoxy ethanol or the like can be used as the aliphatic or aromatic alcohol. A lower aliphatic alcohol such as methanol or ethanol is most preferably used due to its reactivity and low cost.

Further, a phenolic compound can be used in place of the alcoholic compound as the compound which has a hydroxyl (OH) group and reacts with cyclocarbonate to produce the carbonate.

Amorphous aluminosilicate is a well-known material and is usually defined as material with a wide range of pore size and pore size distribution. The material has an anionic framework, like a zeolite, but its three dimensional pore structure is not well defined.

Amorphous aluminosilicate catalysts can include both synthetic and natural materials. Synthetic amorphous aluminosilicate is commercially available and is suitable for the method of the invention. Examples of natural materials include feldspars such as orthoclase $K(AlO_2)(SiO_2)_3$, albite $Na(AlO_2)(SiO_2)_3$, anorthite $Ca(AlO_2)_2 (SiO_2)_2$ and celsian $Ba(AlO_2)_2 (SiO_2)_2$. Further, these naturally existing amorphous aluminosilicates already contain alkali and/or alkaline earth metal. Thus, in such materials, it is not necessary to incorporate the metal into the catalyst, unless an excess stoichiometric amount of metal is desired.

As used in the present application, amorphous aluminosilicate is also defined to include materials that are partially, but not wholly, crystalline. These materials, such as mesopore materials, have a crystalline pore structure with a narrow pore size distribution. Mesopore materials of this type are also well known. Examples of such mesopore materials include MCM41, MCM48 and MCM-50.

A typical amorphous aluminosilicate catalyst has a surface area of 5–1000 $m^2/g$ with no specific limit on $SiO_2/Al_2O_3$ ratio. A high surface area is preferred in the method of the invention, with no specific upper limit. A surface area above 100 $m^2/g$ is most preferred.

Alkali metal is defined as those metals listed in Group 1 (IA) of the Periodic Table of Elements, or a combination thereof Alkaline earth metal is defined as those metals listed in Group 2 (IIA) of the Periodic Table of Elements, or a combination thereof. Preferred alkali metals include potassium, sodium, cesium, or a combination thereof. While the catalytic mechanism is not completely understood, the incorporation of alkali and/or alkaline earth metal into the catalyst creates base sites, which may be catalytically active for the reaction.

Alkali metal and alkaline earth metal are both defined to include compounds containing these metals. The specific limits of the amount of alkali and/or alkaline earth metal which can be incorporated into the catalyst can be determined by one skilled in the art, and will vary based upon the specific catalyst and alkali and/or alkaline earth metal used. The amount of alkali and/or alkaline earth metal can be present in excess of a stoichiometric amount, i.e. the amount of metal required to balance the charges of anionic aluminosilicate framework. However, the amount of alkali and/or alkaline earth metal in the catalyst should not exceed an amount where the pore space of the catalyst is significantly restricted, thereby decreasing the surface area of the catalyst and its activity. Generally, the metal will make up from about 0.1–50 wt %. of the catalyst. For example, if cesium is used as the alkali metal, the amount of cesium will typically be between about 3–50 wt % of the catalyst.

Alkali and/or alkaline earth metal may be incorporated into the aluminosilicate catalyst by any known means. For example, the metal may be incorporated into the framework of the aluminosilicate catalyst via ion exchange. This is a method well known in the art in which protons from the catalyst framework are exchanged with metal cations. If alkali and/or alkaline earth metal is being incorporated in excess of a stoichiometric amount into the catalyst, it is preferred that the incipient wetness impregnation method be used to incorporate the metal. This is another method well known in the art. Another known method for incorporating the metal into the catalyst is ball-milling, wherein the aluminosilicate catalyst and metal are physically milled together to produce a uniform solid mixture. Ball-milling can be used for incorporating either a stoichiometric or excess stoichiometric amount of metal into the catalyst.

The aluminosilicate is the active portion of the catalyst and may be supported on a conventional substrate. Examples of such substrates are silica, alumina, zirconia, titania, and combinations thereof The substrate can be inert or have a mild catalytic activity, but the aluminosilicate should be the major catalytic material driving the transesterification reaction. It is also important that a substrate be chosen that will not create unwanted side reactions.

The reactor type in this invention can be any type generally known such as a continuous fluid bed, fixed bed or stirred tank, etc. Since the catalyst used in the method of the invention is heterogenous, it is preferred that a fixed bed be used so as to avoid the expense of having to recover the catalyst from the reagents.

The reaction conditions of this invention include a reaction temperature of about 20° C. to about 300° C., preferably about 60° C. to about 175° C.; a reaction pressure of about 14 to about 4000 psig, preferably about 50 to about 400 psig; a liquid hourly space velocity of about 0.1 to about 40 $hr^{-1}$, preferably about 0.5 to about 10 $hr^{-1}$; and a molar ratio of alkanol to alkylene carbonate of about 1 to 20, preferably about 2 to 8.

The following examples are provided to assist in a further understanding of the invention. The particular materials and conditions employed are intended to be further illustrative of the invention and are not limiting upon the reasonable scope thereof

EXAMPLE 1

This example describes a method for preparing a catalyst employed in the method of the invention, i.e. amorphous cesium aluminosilicate.

An aqueous solution of cesium carbonate (0.1 N, 3.0 L) was mixed with 75 g of amorphous silica-alumina (Aldrich, 522 $m^2/g$, 6:1 aluminosilicate ratio), and the resultant mixture was stirred at ambient temperature for 6 h. After the cesium carbonate solution was filtered off, the solid catalyst powder was dried in an oven at 120° C. overnight and calcined under nitrogen at 450° C. The calcined catalyst contained 18.1 wt %. cesium and had 375 $m^2/g$ BET surface area.

EXAMPLE 2

A transesterification evaluation was performed for the catalyst described in Example 1.

The transesterification reaction was performed in a fixed bed micro-unit equipped with a three-zone furnace and a down-flow trickle-bed tubular reactor (½" ID). Catalyst powder was pelletized and sized to 60–80 mesh. The reactor was loaded with a mixture of 10 cc of the sized catalyst and 3 cc of 80–120 mesh sand.

After pressure testing of the unit, the catalyst was dried at 400° F. for two hours under 1 atmosphere, 170 cc/min nitrogen flow. At the end of this period, the reactor was cooled down to 150° F. and nitrogen flow was stopped. The reactor pressure, controlled by a pressure regulator, was then set to 100 psig, and the ethylene carbonate (EC)/methanol mixture feed was pumped and added to the top of the reactor at 1.0 h$^{-1}$ LHSV. After the reactor was conditioned for 8 h, the reactor temperature was increased to initial operating temperature. Liquid products were condensed in a stainless steel dropout pot at −10° C. Both liquid and off-gas products were analyzed by GC. The catalytic reaction was studied at various temperatures and LHSV to vary EC conversion.

The catalyst was evaluated according to the procedures described above. Detailed operating conditions and results on EC conversion and dimethyl carbonate (DMC)/ethylene glycol (EG) selectivities for cesium aluminosilicate are summarized in Table 1.

Feed conversion is calculated based on EC converted during the transesterification reaction, since excess amount of methanol (relative to EC) was used for all reactions. During EC/MeOH reaction, 2-hydroxyethyl methyl carbonate (HEMC) intermediate was also formed in addition to DMC and EG. The concentration of HEMC varies depending on the reaction conditions.

Since it is recyclable along with unreacted EC, the intermediate carbonate is not considered as a byproduct. The feed conversion and product selectivity are defined as follows:

EC Conversion=(EC converted to products other than HEMC)/(total EC in feed);

DMC Selectivity=(moles of DMC formed)/(moles of EC converted to products other than HEMC);

EG Selectivity=(moles of EG formed)/(moles of EC converted to products other than HEMC).

TABLE 1

Cesium Aluminosilicate Catalyzed Transesterification of Ethylene Carbonate with Methanol (Condition: 100 psig)

| Temperature, ° F./° C. | 275/135 | 300/149 | 325/163 | 250/121 | 275/135 |
|---|---|---|---|---|---|
| LHSV, h$^{-1}$ | 1.0 | 1.0 | 1.0 | 0.5 | 0.5 |
| Feed Composition | | | | | |
| MeOH/EC, molar ratio | 3.83 | 3.83 | 3.83 | 3.83 | 3.83 |
| Total Liquid Product Composition | | | | | |
| MeOH, wt % | 48.4 | 46.0 | 46.7 | 46.1 | 43.1 |
| EC, wt % | 19.8 | 17.3 | 16.6 | 20.6 | 16.3 |
| HEMC Intermediate, wt %[a] | 11.4 | 7.3 | 6.1 | 7.6 | 8.7 |
| DMC, wt % | 11.6 | 16.9 | 16.9 | 14.7 | 17.9 |
| EG, wt % | 8.8 | 12.2 | 11.8 | 11.0 | 13.9 |
| DMC/EG, Molar Ratio | 0.91 | 0.96 | 0.99 | 0.92 | 0.89 |
| EC Conv., % | 30.8 | 43.2 | 46.3 | 37.3 | 46.6 |
| DMC Select., % | 90.5 | 96.1 | 90.9 | 92.5 | 88.5 |
| EG Select., % | 99.5 | 100.0 | 92.0 | 100.0 | 99.6 |

[a]HEMC: 2-hydroxyethyl methyl carbonate-an intermediate carbonate formed during the reaction of ethylene carbonate with methanol.

The examples demonstrate that the transesterification catalysts of the current invention exhibit good activity and high selectivity in the reaction of alkylene carbonate with alkanol.

More specifically, cesium aluminosilicate demonstrated an EC conversion of approximately 37–47% within the operating temperatures of 250° F.–325° F. In general, the conversion increases with increasing temperature at constant liquid hourly space velocity. The DMC selectivity was between approximately 89–96% for the full range of tested operating temperatures, i.e. 250° F.–325° F. The EG selectivity was even greater at about 100% for the operating temperatures of 250–300° F.

Therefore, the method of the invention is adaptable to commercial application because of the good level of activity, high selectivity over a wide temperature range, and the stability and relatively low cost of the aluminosilicate catalyst used.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A method of co-producing dialkyl carbonate and alkanediol comprising reacting alkylene carbonate with alkanol in the presence of an amorphous aluminosilicate catalyst, said catalyst comprising alkali metal, alkaline earth metal, or a combination thereof.

2. A method as described in claim 1 wherein said alkylene carbonate is ethylene carbonate.

3. A method as described in claim 1 wherein said alkanol is methanol.

4. A method as described in claim 1 wherein said alkali metal is cesium.

5. A method as described in claim 1 wherein said alkali metal, alkaline earth metal, or combination thereof is present in said catalyst in a stoichiometric amount.

6. A method as described in claim 1 wherein said alkali metal, alkaline earth metal, or combination thereof are present in said catalyst in excess of a stoichiometric amount.

7. A method as described in claim 1 wherein said alkali metal, alkaline earth metal, or combination thereof is present in said catalyst in an amount of about 0.1 to about 50 wt %.

8. A method as described in claim 1 wherein said catalyst has a surface area above 100 m$^2$/g.

9. A method as described in claim 1 wherein said catalyst is supported on a substrate.

10. A method as described in claim 1 wherein said process conditions comprise a reaction temperature of about 20° C. to about 300° C., a reaction pressure of about 14 to about 4000 psig, a liquid hourly space velocity of about 0.1 to about 40 hr$^{-1}$, and a molar ratio of alkanol to alkylene carbonate of about 1–20.

* * * * *